US009386951B2

(12) United States Patent
Sánchez et al.

(10) Patent No.: US 9,386,951 B2
(45) Date of Patent: *Jul. 12, 2016

(54) METHOD AND APPARATUS FOR MONITORING SLEEP APNEA SEVERITY

(75) Inventors: Roberto Hornero Sánchez, Valladolid (ES); José Victor Marcos Martín, Valladolid (ES); Daniel Álvarez González, Valladolid (ES); Pedro Mateo Riobo Aboy, Portland, OR (US); Félix del Campo Matías, Valladolid (ES)

(73) Assignee: UNIVERSIDAD DE VALLADOLID, Valladolid (ES)

( * ) Notice: Subject to any disclaimer, the term of this patent is extended or adjusted under 35 U.S.C. 154(b) by 773 days.

This patent is subject to a terminal disclaimer.

(21) Appl. No.: 13/561,011

(22) Filed: Jul. 28, 2012

(65) Prior Publication Data

US 2012/0296182 A1  Nov. 22, 2012

Related U.S. Application Data

(63) Continuation-in-part of application No. 13/044,846, filed on Mar. 10, 2011, now Pat. No. 8,862,195.

(60) Provisional application No. 61/523,403, filed on Aug. 15, 2011, provisional application No. 61/312,252, filed on Mar. 10, 2010.

(51) Int. Cl.
*A61B 5/1455* (2006.01)
*A61B 5/00* (2006.01)

(52) U.S. Cl.
CPC .......... *A61B 5/4818* (2013.01); *A61B 5/14551* (2013.01); *A61B 5/7264* (2013.01)

(58) Field of Classification Search
CPC . A61B 5/4818; A61B 5/7264; A61B 5/14551
See application file for complete search history.

(56) References Cited

U.S. PATENT DOCUMENTS 7,309,314 B2   12/2007   Grant et al.
7,706,852 B2 *  4/2010   Baker, Jr. ............... 600/323

(Continued)

OTHER PUBLICATIONS

J. Victor Marcos et al., Automated Prediction of the Apnea-Hypopnea Index from Nocturnal Oximetry Recordings. IEEE Transactions on Biomedical Engineering, vol. 59, No. 1, Jan. 2012.

*Primary Examiner* — Eric Winakur
(74) *Attorney, Agent, or Firm* — Mateo Aboy; Aboy & Associates, PC

(57) ABSTRACT

Disclosed embodiments include a method and an apparatus for monitoring sleep apnea severity that comprise: (a) analyzing an oxygen saturation signal to extract a plurality of time-domain and frequency-domain metrics; (b) calculating an oxygen saturation-based Apnea Hyponea Index (AHI) by employing a predetermined functional mapping between said metrics and polysomnography (PSG)-based AHI; and (c) displaying an oxygen saturation-based AHI to enable a specialist to monitor sleep apnea severity without requiring PSG. According to a particular embodiment, the oxygen saturation signal is nocturnal oxygen saturation and the functional mapping is a multilinear regression model (MLR) or a multilayer perceptron network (MLP).

18 Claims, 10 Drawing Sheets

(56) References Cited

U.S. PATENT DOCUMENTS 7,785,262 B2  8/2010  Melker et al.
2005/0131283 A1  6/2005  Grant et al.
2006/0241506 A1  10/2006  Melker et al.

* cited by examiner

CLINICAL AND DEMOGRAPHIC DATA FOR TRAINING AND TEST SETS

|  | TRAINING SET | TEST SET |
|---|---|---|
| SUBJECTS | 96 | 144 |
| AGE (YEARS) | 52.35 ± 13.76 | 52.19 ± 13.73 |
| MALES (%) | 77.08 | 77.78 |
| BMI (Kg/m²) | 29.83 ± 4.17 | 29.83 ± 4.53 |
| AHI (h⁻¹) | 24.75 ± 25.19 | 26.39 ± 26.74 |

FIG.9

COEFFICIENTS OF THE MLR MODEL DERIVED FROM THE TRAINING SET

| FEATURE | COEFFICIENT | FEATURE | COEFFICIENT |
|---|---|---|---|
| $\mu_S$ | −2.39 | $\mu_F$ | 14.41 |
| $\sigma_S$ | −6.74 | $\sigma_F$ | 0.95 |
| $\gamma_S$ | −0.73 | $\gamma_F$ | 3.23 |
| $\delta_S$ | −5.55 | $\delta_F$ | 0.90 |
| ApEn | −4.54 | $S_T$ | 13.45 |
| CTM | −11.49 | $S_B$ | −27.08 |
| LZC | 6.08 | PA | 14.38 |

FIG.10

DIAGNOSTIC RESULTS ACHIEVED BY MLR AND MLP REGRESSION MODELS

| MLR | | | | |
|---|---|---|---|---|
| TRUE | PREDICTED | | | |
| | No SAHS | MILD | MODERATE | SEVERE |
| No SAHS | 21 | 11 | 2 | 0 |
| MILD | 10 | 11 | 10 | 1 |
| MODERATE | 1 | 2 | 17 | 10 |
| SEVERE | 0 | 0 | 3 | 45 |

| MLP | | | | |
|---|---|---|---|---|
| TRUE | PREDICTED | | | |
| | No SAHS | MILD | MODERATE | SEVERE |
| No SAHS | 20 | 14 | 0 | 0 |
| MILD | 8 | 18 | 6 | 0 |
| MODERATE | 1 | 3 | 21 | 5 |
| SEVERE | 0 | 0 | 3 | 45 |

FIG.11

DIAGNOSTIC RESULTS USING A BINARY CLASSIFICATION APPROACH

| | MLR | | | MLP | | |
|---|---|---|---|---|---|---|
| AHI ($h^{-1}$) | 5 | 10 | 15 | 5 | 10 | 15 |
| Se (%) | 90.00 | 89.58 | 96.15 | 91.82 | 89.58 | 94.87 |
| Sp (%) | 61.76 | 77.08 | 80.30 | 58.82 | 81.25 | 90.91 |
| Acc (%) | 83.33 | 85.42 | 88.89 | 84.03 | 86.81 | 93.06 |

Se: SENSITIVITY; Sp: SPECIFICITY; Acc: ACCURACY.

FIG.12

METHOD AND APPARATUS FOR MONITORING SLEEP APNEA SEVERITY

CROSS-REFERENCE TO RELATED APPLICATIONS

This application claims the priority benefit of U.S. Provisional Application No. 61/523,403 filed on 2011 Aug. 15 by the present inventors, and is a continuation-in-part of U.S. Nonprovisional application Ser. No. 13/044,846 filed on 2011 Mar. 10 which claims the priority benefit of U.S. Provisional Application No. 61/312,252 filed on 2010 Mar. 10, which are all incorporated herein by reference in their entirety.

TECHNICAL FIELD

This invention relates to methods, systems, and apparatuses for sleep apnea monitoring. Specifically, it relates to methods, systems, and apparatuses for calculating the apnea-hypopnea index from oximetry signals.

BACKGROUND

The sleep apnea-hypopnea syndrome (SAHS) is characterized by repetitive complete (apnea) or partial (hypopnea) collapse of the upper airway during sleep. Apnea events are associated to hypoxemia, heart rate variations and arousals. Epidemiological data support the finding that SAHS may have a role in the initiation or progression of diverse respiratory, cardiovascular, and cerebrovascular diseases. The incidence of SAHS has been estimated at 5% of adults in western countries. Furthermore, previous studies revealed that a high percentage of patients (82% of men and 93% of women) with moderate or severe SAHS might remain undiagnosed. Therefore, early detection and treatment of SAHS are required in order to prevent long-term effects and end-organ damages.

Nowadays, nocturnal polysomnography (PSG) is the gold-standard for SAHS diagnosis. PSG studies are performed in special sleep units and generally involve monitoring several physiological recordings such as electrocardiograms (ECG), electroencephalograms (EEG), electromyograms (EMG), electrooculograms (EOG), airflow signals, respiratory effort, and oxygen saturation (SaO2) or oximetry. These signals are typically manually analyzed by a sleep specialist in order to identify every episode of apnea/hypopnea. The number of detected events is divided by the hours of sleep to compute the apnea-hypopnea index (AHI), which is used to assess SAHS severity. However, PSG studies have drawbacks since they are costly, time-consuming, and require subjects to be overnight in a special medical facility. Additionally, the demand for PSG studies is progressively growing as people and clinicians are becoming aware of SAHS whereas the available infrastructure is insufficient to support it. Consequently, new methods, apparatuses and systems focused on alternative diagnostic methods that overcome some of the limitations associated to PSG are needed.

Related art includes U.S. patent application Ser. No. 10/947,983 which discloses a method for diagnosing OSAS based on a tool for the predicting Apnea Hypopnea Index (AHI) using non-parametric analysis and bootstrap aggregation, and U.S. patent application Ser. No. 11/122,278 which discloses a method for monitoring respiration involving processing plethysmography signals.

New techniques for simplified SAHS detection have been commonly based on the analysis of a reduced set of data. The utility of clinical and demographic variables, as well as ECG has been studied by the research community. In the context of this problem, SaO2 signals recorded through nocturnal pulse oximetry are of special interest since they can be easily acquired and enable for portable monitoring. Pulse oximetry is a non-invasive technique used to monitor arterial blood oxygen saturation. Oximetry recordings contain essential information about SAHS and play a crucial role to interpret PSG studies. Apneas and hypopneas are usually accompanied by marked desaturation events due to the lack of airflow. As a result, patients with SAHS tend to present unstable SaO2 signals due to frequent drops in the saturation value. A different behavior tends to be observed in healthy patients. Their recordings reflect normal ventilation, which corresponds with a saturation value near 90% and the absence of repetitive abrupt changes in the SaO2 profile.

Improved methods and the corresponding apparatuses are still needed in order to provide more accurate models that characterize SAHS from SaO2 signals, especially to determine the severity of SAHS.

SUMMARY

Disclosed embodiments include a method for monitoring sleep apnea severity that comprises: (a) analyzing an oxygen saturation signal to extract a plurality of time-domain and frequency-domain metrics; (b) calculating an oxygen saturation-based Apnea Hyponea Index (AHI) by employing a predetermined functional mapping between said metrics and polysomnography (PSG)-based AHI; and (c) displaying an oxygen saturation-based AHI to enable a specialist to monitor sleep apnea severity without requiring PSG. According to a particular embodiment, the oxygen saturation signal is nocturnal oxygen saturation and the functional mapping is a multilinear regression model (MLR) or a multilayer perceptron network (MLP) with more than 20 hidden nodes. More particularly, the time-domain metrics comprise nonlinear methods that measure irregularity, variability, and complexity of said oxygen saturation signal such as approximate entropy (ApEn), Lempel-Ziv complexity (LZC), and central tendency measure (CTM). Similarly, embodiments of apparatuses for monitoring sleep apnea severity are disclosed. Disclosed embodiments include an apparatus that comprises: (a) a processor configured for 1) analyzing an oxygen saturation signal to extract a plurality of time-domain and frequency-domain metrics and 2) calculating an oxygen saturation-based Apnea Hyponea Index (AHI) by employing a predetermined functional mapping between said metrics and polysomnography (PSG)-based AHI; and (b) an output device configured for displaying an oxygen saturation-based AHI to enable a specialist to monitor sleep apnea severity without requiring PSG. According to a particular embodiment of the apparatus, the oxygen saturation signal is nocturnal oxygen saturation and the functional mapping is a multilinear regression model (MLR) or a multilayer perceptron network (MLP) with more than 20 hidden nodes.

BRIEF DESCRIPTION OF THE DRAWINGS

Disclosed embodiments are illustrated by way of example, and not by way of limitation, in the figures of the accompanying drawings.

FIG. 7-12 show information related to experimental studies conducted to design and validate the AHI calculation method.

DETAILED DESCRIPTION

Figure 6:
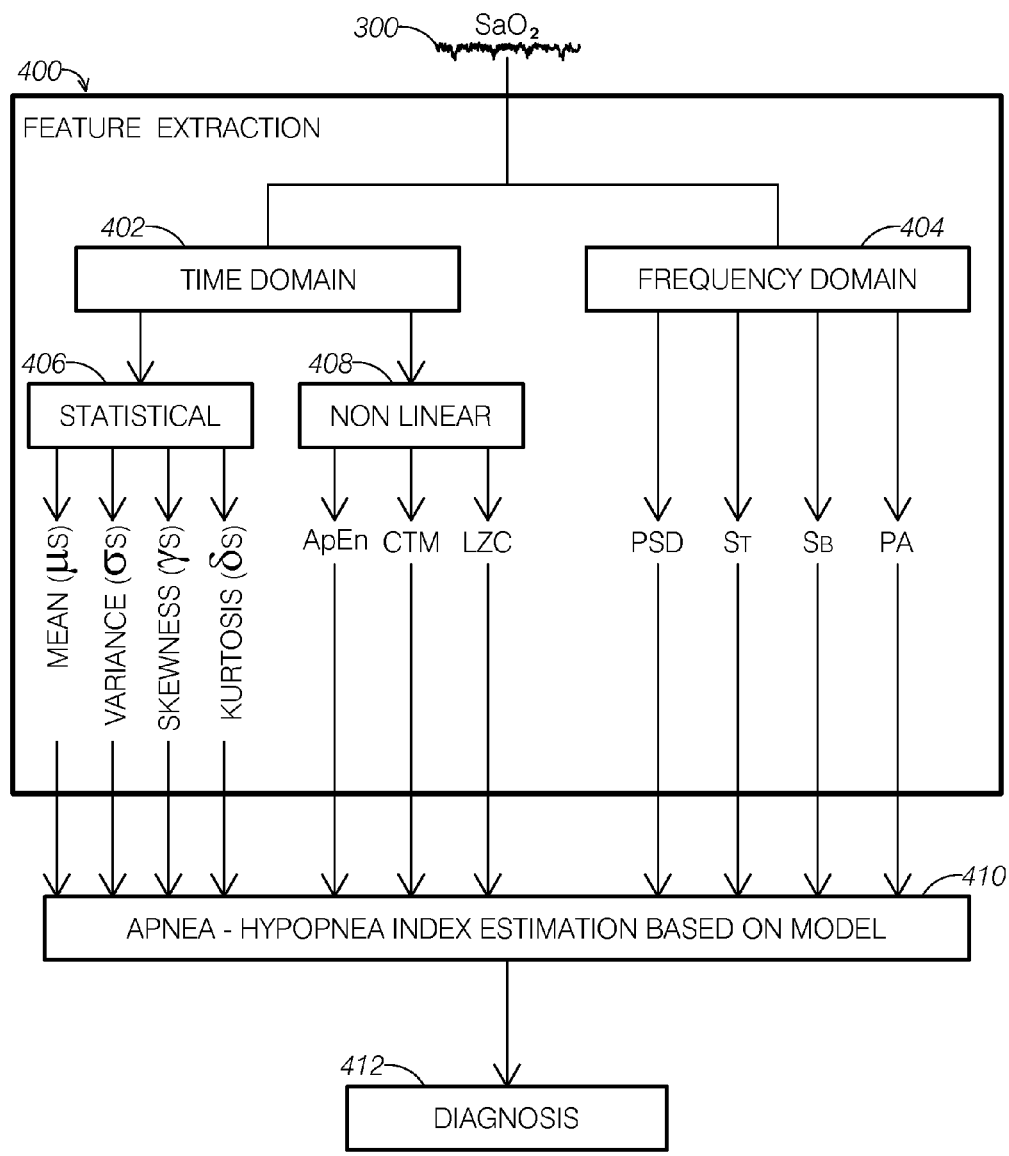
FIG. 6 shows a block diagram of the AHI calculation method according to one embodiment.

The detailed description discloses embodiments directed to: 1) a method and an apparatus for detection of sleep apnea (FIGS. 1-3), and 2) a method and apparatus for calculation of AHI (FIG. 6). Section A describes embodiments of the method and apparatus for detection of sleep apnea. Section B describes embodiments of the method and apparatus for calculation of AHI.

A. Method and Apparatus Description for Detection of Sleep Apnea

A.1. Overall Method and System Description

Figure 1:
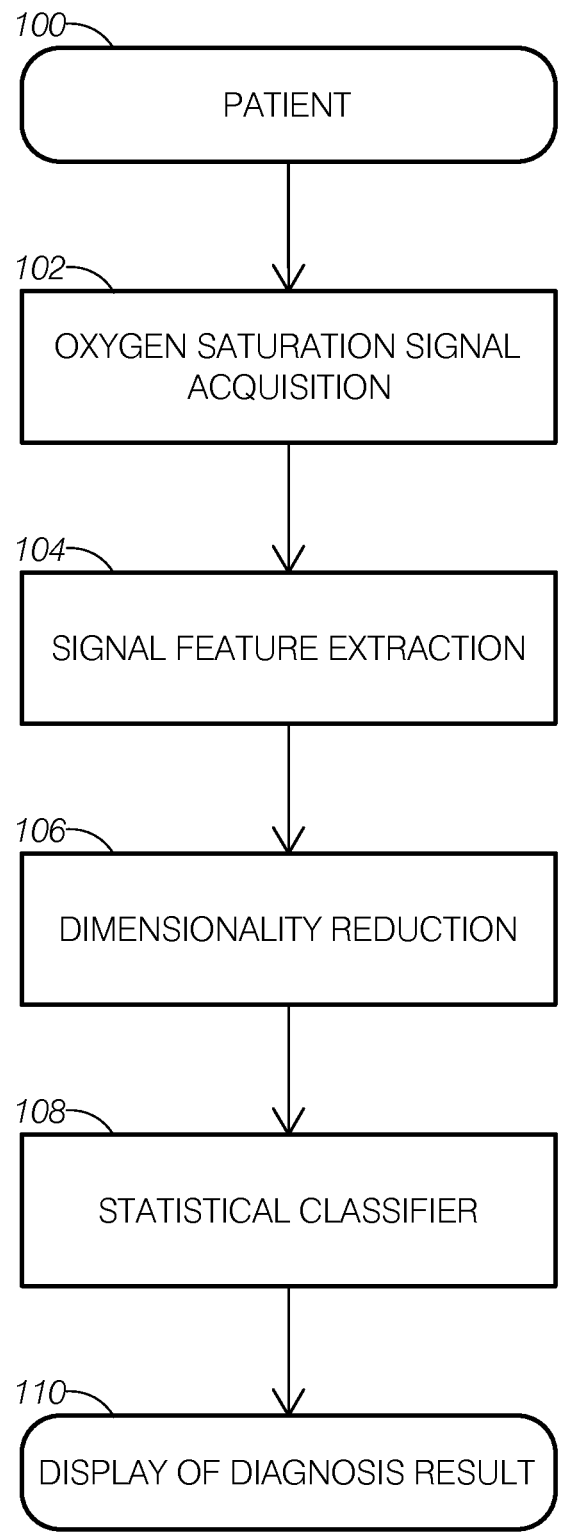
FIG. 1 shows a block diagram of the detection method according to one embodiment.

FIG. 1 shows a block diagram of the method according to one embodiment. Disclosed embodiments include a method for automatic detection of sleep apnea implemented in a medical apparatus including an oxygen saturation signal acquisition circuit 102, one or more processors, one or more memories, and one or more displays; the method comprising: (a) extracting a plurality of signal features by analyzing an oxygen saturation signal acquired by the signal acquisition hardware 104; (b) performing dimensionality reduction on the plurality of signal features to generate a plurality of signal features in a transformed space 106; and (c) displaying a sleep apnea diagnosis result 110 on the displays of the medical apparatus based on a statistical classifier 108 that operates on the plurality of signal features in a transformed space.

Figure 2:
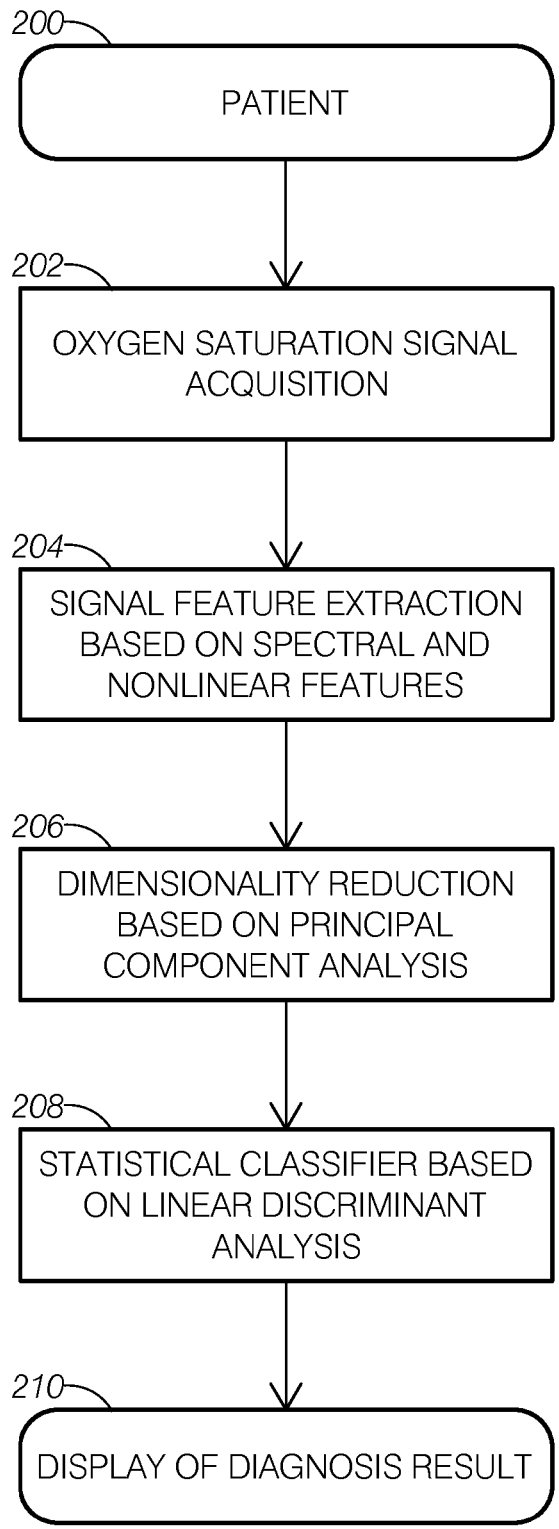
FIG. 2 shows a block diagram of the detection method according to a particular embodiment.

FIG. 2 shows a block diagram of the method according to a particular embodiment. According to this particular embodiment, and without limitation, the signal features include a plurality of spectral metrics based on power spectral density and a plurality of nonlinear metrics 204 including Approximate Entropy, Central Tendency Measure, and Lempel-Ziv complexity. The dimensionality reduction is performed by a method substantially equivalent to principal component analysis 206 and the statistical classifier is substantially equivalent to linear discriminant analysis 208. Alternative embodiments may employ other statistical classifiers including quadratic discriminant analysis, k-nearest neighbors, and logistic regression.

According to a specific embodiment, the method can be implemented in a medical system with one or more processors, physiological signal acquisition, analog-to-digital and digital-to-analog converters, one or more memories, and one or more output displays such as the typical bedside monitors used in clinical settings. Alternatively, it can be implemented in a digital computer with one or more processors to analyze physiological signals and display the results, output the results in the form of a printed or electronic clinical report, or send the results over a network to a receiving node for further clinical analysis and use. Consequently, in this disclosure we present a method for automatic detection or diagnosis of sleep apnea. Such method can be implemented in a stand-alone medical apparatus such as a bedside monitor with the hardware elements disclosed above. Alternatively, it may be implemented as a system that includes a plurality of methods, apparatuses, and a networks infrastructure.

A.2. Detailed Method and System Description

Figure 3:
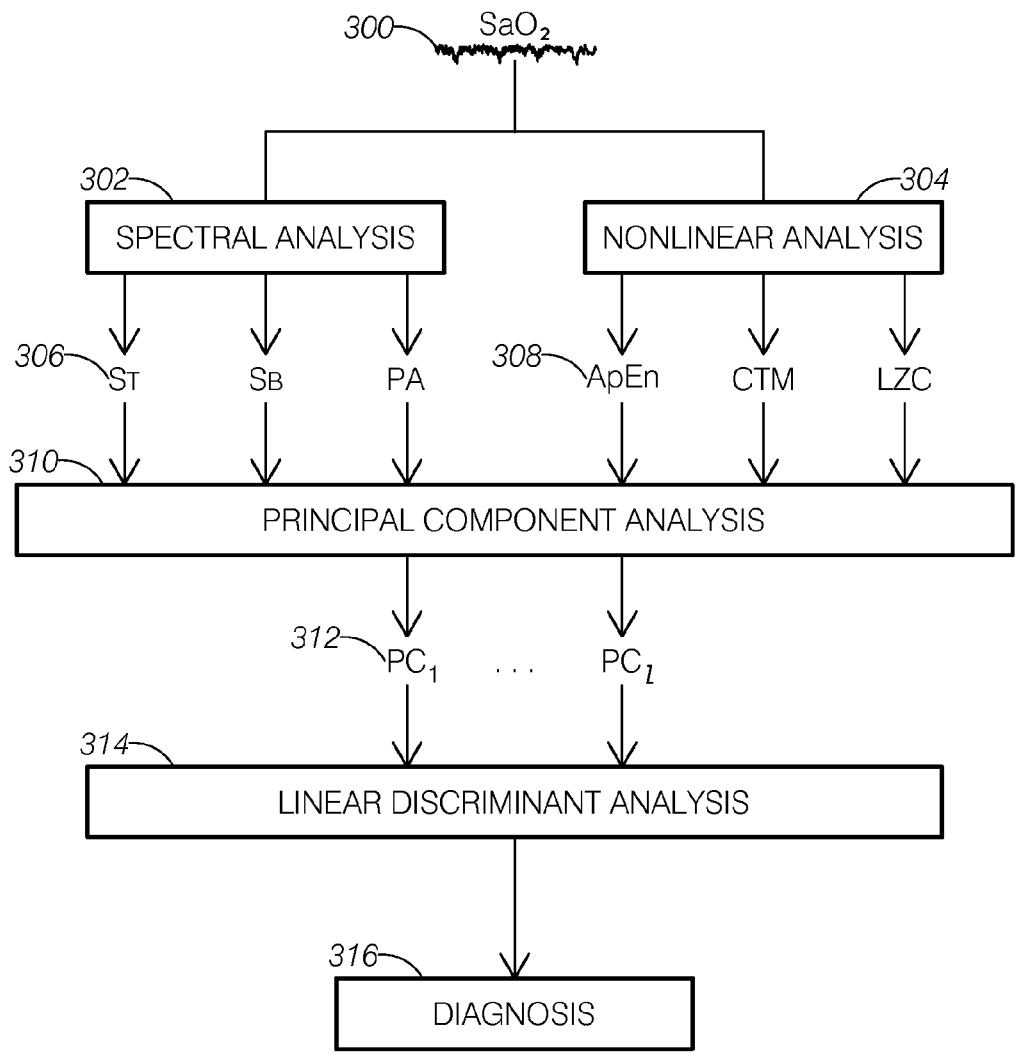
FIG. 3 shows a block diagram of the detection method according to a particular embodiment.

FIG. 3 shows a block diagram of the method according to a particular embodiment including additional implementation details. The following sections describe a detailed description of the method according to one particular embodiment disclosed herein to illustrate one possible reduction to practice by way of example. While particular embodiments are described, it is understood that, after learning the teachings contained in this disclosure, modifications and generalizations will be apparent to those skilled in the art without departing from the spirit of the disclosed embodiments.

A.2.1. Step 1—Feature Extraction

The feature extraction stage maps the SaO2 signal 300 into a reduced set of variables or features to summarize the information in the recording. The extracted features measure relevant properties of oximetry data in order to discriminate signals from OSAS positive subjects. Spectral 302 and nonlinear 304 analyses of SaO2 signals 300 provide valuable information to detect OSAS. Statistically significant differences were found between OSAS positive and negative subjects by evaluating different spectral and nonlinear features. Consequently, according to one embodiment our proposed automatic OSAS detection method uses both spectral analysis and nonlinear analysis for feature extraction.

A.2.1.1. Spectral Analysis

Periodicities of ventilation originate phase-lagged changes in SaO2 data 300. The duration of apnea events ranges from 30 s to 2 min, including the awakening response after the event. These events are reflected in oximetry recordings by a fluctuation (decrease and subsequent restoration of the saturation value) with the same duration. The recurrence of apneas during sleep infers some periodic behavior in SaO2 signals 300. Due to the duration of the events, the repetition of changes in these signals occurs with a rate between 30 s and 2 min. The frequency band associated to these periods of fluctuation ranges between 0.010 and 0.033 Hz. Thus, the signal power contained in this band is usually higher in subjects with OSAS than in controls.

According to a particular embodiment, and without limitation, the proposed OSAS detection method calculates the following spectral features 306 computed from the power spectral density (PSD) 302 of SaO2 data 300:

Feature 1. Total area under the PSD ($S_T$). This feature provides an estimate of the signal power.

Feature 2. Area enclosed in the band of interest ($S_B$). This feature approximates the amount of signal power contained in the band between 0.010 and 0.033 Hz.

Feature 3. Peak amplitude of the PSD in the band of interest ($P_A$). It represents the most significant frequency component contained in the band between 0.010 and 0.033 Hz.

According to the dynamical behavior of SaO2 recordings 300, these spectral features 306 are expected to be higher in signals corresponding to OSAS positive subjects. However, alternative frequency ranges can be used with correlated results.

A.2.1.2. Nonlinear Analysis

SaO2 signals 300 from patients affected by OSAS tend to present frequent changes and fluctuations due to the repetition of apneas. In contrast, oximetry recordings corresponding to control subjects tend to have a near-constant value of saturation around 97%. Nonlinear analysis 304 of oximetry data can capture these differences, representing a useful means to quantitatively distinguish OSAS patients from control subjects. According to a particular embodiment, and without limitation, the proposed OSAS detection method calculates the following nonlinear metrics 308 from the SaO2 recordings during the feature extraction stage:

Feature 4. Approximate entropy (ApEn). It provides an estimate of the irregularity of a signal. High values of ApEn correspond to irregular signals. Two input parameters must be specified to compute ApEn: a run length m and a tolerance window r. Briefly, ApEn measures the logarithmic likelihood that runs of patterns that are close (within r) for m contiguous observations remain close (within the same tolerance width r) on subsequent incremental comparisons.

Feature 5. Central tendency measure (CTM). It quantifies the variability of a time series, assigning low values to signals with a high degree of chaos. Second-order difference plots are generated by plotting $(s_{t+2}-s_{t+1})$ vs. $(s_{t+1}-s_t)$, where $s_t$ is the time series of length T. Then, CTM is computed by selecting a circular region of radius r round the origin, counting the number of points that fall within the radius and dividing by the total number of points.

Feature 6. Lempel-Ziv complexity (LZC). It is a non-parametric, simple-to-calculate measure of complexity in a one-dimensional signal. Complex signals generate high values of LZC. This feature is related to the number of distinct substrings and the rate of their recurrence along a given sequence. The signal must be transformed into a finite symbol sequence before calculating the complexity measure. The transformation is carried out by comparing each sample with a fixed threshold. Usually, the median value is used to obtain a 0-1 sequence. Then, this binary sequence is scanned from left to right and the complexity counter is increased by one unit every time a new subsequence of consecutive characters is encountered.

The presence of OSAS is related to irregularity, variability and complexity of SaO2 measured by ApEn, CTM and LZC 308, respectively. As a result, high values of ApEn and LZC as well as low CTM values are expected for recordings from OSAS positive subjects.

A.2.2. Step 2—Preprocessing: Principal Component Analysis (PCA)

According to a particular embodiment, once the method obtains the spectral ($S_T$, $S_B$, PA) 306 and nonlinear features (ApEn, CTM, LZC) 308 during the feature extraction stage, it performs PCA 310 before the pattern classification stage 314. PCA is usually applied to perform dimensionality reduction. Vectors x in a d-dimensional space are mapped into a l-dimensional space, where $l \leq d$ is determined according to a given criterion. Samples of variable x in the original space are defined by the spectral and nonlinear features from SaO2 recordings (d=6). PCA produces an uncorrelated set of d variables or components by projecting the input data onto the eigenvectors of the covariance matrix of variable x. These eigenvectors constitute an orthonormal basis in the original space. Additionally, the new d components are ranked by PCA in decreasing importance since the amount of variance along a particular eigenvector is represented by its associated eigenvalue. In this embodiment the method proceeds as follows:

1. The mean of the vectors in the original space is computed and subtracted.
2. The covariance matrix is calculated and its eigenvectors and eigenvalues are found.
3. The eigenvectors corresponding to the/largest eigenvalues are retained.
4. The original vectors are projected onto the eigenvectors to give the components of the transformed vectors in the l-dimensional space.

Each component obtained from PCA is a linear combination of features in the original space and the first l components are selected to define the dimension of the transformed space.

A.2.3. Step 3—Classification: Linear Discriminant Analysis (LDA)

In this step, the variables selected 312 from PCA 310 are the inputs to the statistical classifier based on LDA 314. Classifiers based on LDA makes two prior hypotheses about the statistical distribution of the input variables. First, the distributions of samples in both classes are required to be normal. Additionally, it is supposed that all the class covariance matrices are identical (homocedasticity). Applying PCA to the spectral and nonlinear parameters results in input variables that better satisfy the statistical requirements of LDA. Alternative embodiments may employ other statistical classifiers including quadratic discriminant analysis, k-nearest neighbors, and logistic regression.

While particular embodiments have been described, it is understood that, after learning the teachings contained in this disclosure, modifications and generalizations will be apparent to those skilled in the art without departing from the spirit of the disclosed embodiments.

A.2.4. Example Performance Results

Figure 4:
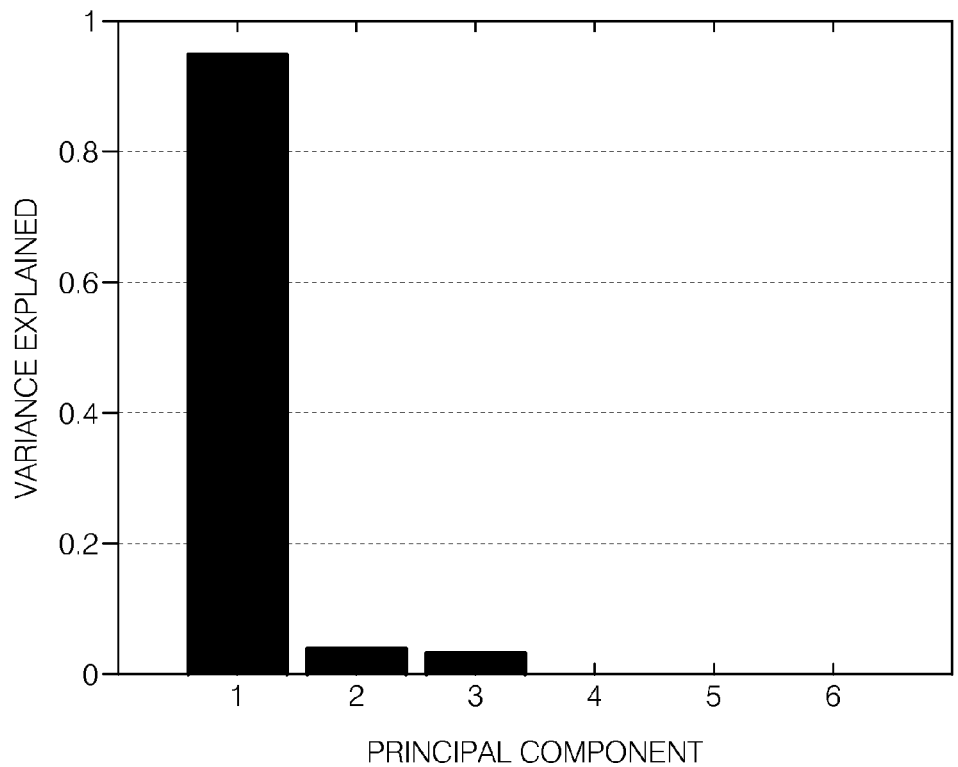
FIG. 4 shows the results of a study to determine the variance explained by the principal components in the detection method.
Figure 5:
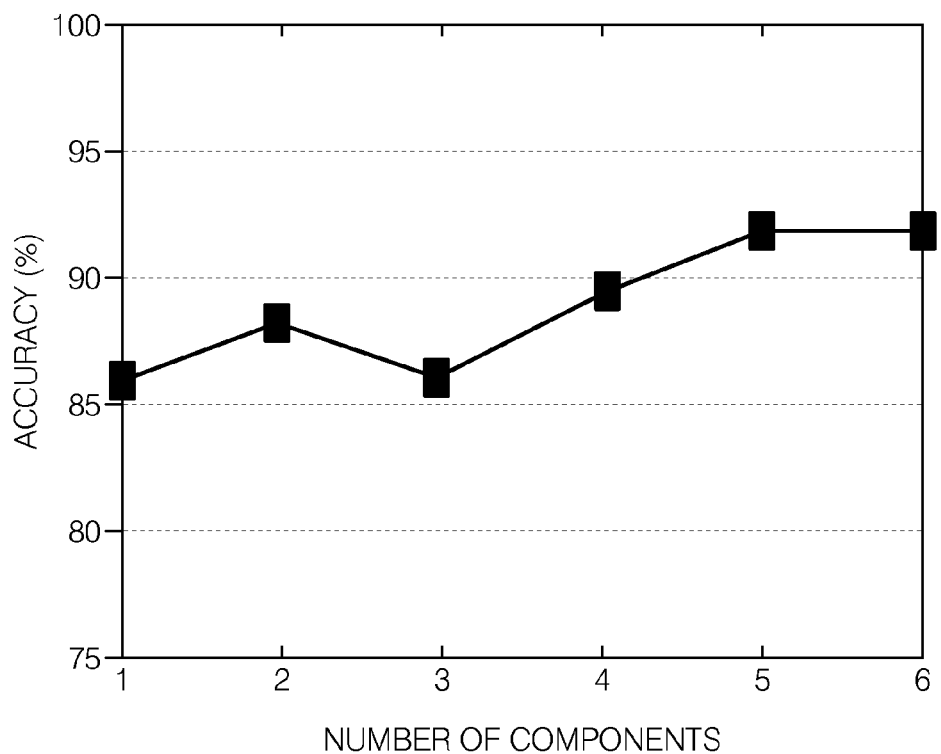
FIG. 5 shows the results of a study to determine the accuracy of a particular embodiment of the detection method.

A validation study was conducted to evaluate the performance of a particular embodiment of the OSA detection method, system, and apparatus. The results of this assessment study to evaluate a particular embodiment of the computer-implemented method described herein have been reported in the peer-reviewed article entitled "Automated detection of obstructive sleep apnea syndrome from oxygen saturation recordings using linear discriminant analysis" published in Med Biol Eng Comput. 2010 September; 48(9):895-902. Specifically, a scientific study was conducted to characterize and prospectively validate a particular embodiment of the proposed OSAS detection algorithm. The population under study was composed of subjects suspected of suffering from OSAS. A total of 214 SaO2 signals were used. These signals were randomly divided into a training set (85 signals) and a test set (129 signals) to prospectively validate the proposed method and system. The OSAS detection algorithm achieved a diagnostic accuracy of 93.02% (97.00% sensitivity and 79.31% specificity) on the test set. It outperformed other alternative implementations that either use spectral and non-linear features separately or are based on logistic regression (LR). The proposed method could be a useful tool to assist in early OSAS diagnosis, contributing to overcome the difficulties of conventional PSG. FIG. 4 shows the results of a study to determine the variance explained by the principal components. FIG. 5 shows the results of a study to determine the accuracy of a particular embodiment of the method.

B. Method and System Description for Prediction of the AHI

B.1. Overall Method and System Description

FIG. 6 shows a block diagram of the AHI calculation method according to one embodiment. The method is comprised of a feature extraction module 400, and a second module that includes a model for estimation of AHI 410. According to one embodiment, the feature extraction module comprises time domain 402 and frequency domain 404 features designed to characterize the SaO2 input signal 300. In one embodiment, the time domain 402 features include both statistical 406 and nonlinear 408 metrics. According to one embodiment, the method is implemented in an apparatus containing at least one processor, one memory, and one input-output device. The processor can be configured to execute the method steps in order to analyze and process the input SaO2 signals and estimate the AHI for a particular subject.

B.2. Detailed Method and System Description

The proposed method comprises two different stages. In the first one, feature extraction from SaO2 data is carried out in order to capture the dynamical behavior of the signal. The second stage corresponds to a model for determining the AHI as a function of the extracted features.

B.2.1 Feature Extraction

According to one embodiment, in the feature extraction phase, information in the SaO2 recording is summarized into a reduced set of measurements or features. These features are defined in order to represent different signal properties related to the degree of SAHS severity. Domain knowledge about the influence of apnea events on SaO2 dynamic is used to define a set of 14 measurements. According to the domain used for SaO2 analysis, the extracted features are divided into two groups: time-domain 402 and frequency-domain 404 features.

B.2.1.1 Time-Domain Analysis

According to one embodiment, the method uses time-domain statistics 402 as features for the model. Marked drops in the amplitude of oximetry signals reflect desaturation events due to apneas. Subjects with low AHI are expected to present SaO2 tracings with minor oscillations around 96% during most of the time. In contrast, a high AHI reflects the repetition of apneas, resulting in SaO2 recordings with marked instability. In an embodiment, statistics and non-linear methods are used to characterize this dynamic behavior in the time domain. The distribution of SaO2 values tends to reflect different properties depending on the AHI. Mean, variance, skewness and kurtosis are computed to quantify the central tendency, the degree of dispersion, the asymmetry and the peakedness, respectively, for the SaO2 signal.

According to one embodiment, in addition to the above mentioned statistics 406, SaO2 signal is also analyzed using nonlinear methods 408 by means of approximate entropy (ApEn), central tendency measure (CTM) and Lempel-Ziv complexity (LZC) in order to measure irregularity, variability and complexity, respectively. Our research indicates that these properties are usually more pronounced in oximetry recordings from subjects with higher AHI.

Oximetry recordings are generally non-stationary. Thus, according to one embodiment, and without limitation, each time-domain feature is computed by dividing the signal into 512-sample epochs, computing the value of the feature for each epoch and averaging over all the epochs. Several design parameters must be adjusted for the proposed nonlinear methods. In an example embodiment, these are set as follows: for the case of ApEn, the sequence length m is set to 1 while the width of the tolerance window r is fixed at 0.25 times the standard deviation of the samples in each signal epoch. To compute CTM, a radius is selected. Finally, LZC is computed by converting SaO2 samples in each epoch into a 0-1 sequence. Each sample is compared with the median value from the epoch to transform the data B.2.1.2 Frequency-Domain Analysis According to one embodiment, the method also uses frequency domain metrics 404. In a particular embodiment, and without limitation, the non-parametric Welch's method is used to compute the power spectral density (PSD) of oximetry recordings. The original SaO2 series is divided into M overlapping sequences of length L by applying a window function.

The modified periodogram is computed for each of them by using the Fast Fourier Transform (FFT). A 512-sample Hanning window and 5% overlapping are applied to estimate the PSD of SaO2 signals using the Welch's method. The length of the FFT for each signal segment is set to 1024 samples. Alternative embodiments may use other nonparametric PSD estimation methods (e.g., Blackman-Tukey) or parametric methods.

According to one embodiment, statistical analysis is conducted in order to characterize the spectral properties of the signal. In this embodiment, the normalized PSD is used as the probability density function, and mean, variance, skewness, and kurtosis are computed.

According to an embodiment, in order to reflect the incidence of apnea events, three additional features are derived from the PSD function: the total power of the SaO2 signal ($S_T$), the power in the band between 0.010 and 0.033 Hz ($S_B$), and the most significant frequency component in that band ($P_A$) 404.

In one embodiment, prior to regression analysis, each of the extracted features is normalized to have a zero mean and unit variance distribution in order to avoid differences between their magnitudes.

B.2.2. AHI Estimation Based on Model

The extracted features in the previous step are used as inputs for a model that relates the AHI with the set of SaO2 features.

According to one embodiment, and without limitation, the model is based on multilinear regression (MLR) using the coefficients shown in FIG. 10 for each of the features.

In an alternative embodiment, the AHI estimation model is based on a multilayer perceptron (MLP) network.

The details of how to develop the MLR-based and the MLP-based models are disclosed in the next section, which explains the experimental study conducted to determine the relationship between the set of SaO2 features obtained during feature extraction 400 and the AHI.

C. Experimental Methodology for Determining the Model Parameters

This section describes the experimental methodology conducted in order to determine the model parameters. It describes an example of the scientific study that was necessary in order to determine how the extracted features relate to the AHI.

Regression techniques were used to estimate the function relating the AHI to the set of SaO2 features. A one dimensional continuous variable (t) was used to model the AHI value (target variable). The extracted features were grouped into a pattern $x=(x_1, x_2, \ldots, x_d)$ representing the multivariate independent variable. The approximation is built from a finite training set D composed of N input-output independent pairs $\{(x_n, t_n)\}_{n=1}^{N}$. Training samples are assumed to satisfy the following condition:

$$t_n = h(x_n) + \epsilon_n \tag{1}$$

Regression techniques define a mapping function y(x, w) that represents an approximation to h(•), where w denotes a set of model adaptive parameters or weights. According to the maximum likelihood principle, these weights must be chosen in order to minimize the sum-of-squares error between the actual and estimated AHI for pattern. As a result, the output of the model approximates the conditional average of the target data.

The performance of two regression techniques was studied: MLR and MLP networks.

C.1. Multiple Linear Regression

MLR models assume a linear expression for the regression function. Thus, the mapping implemented by the algorithm takes the form:

$$y(x,w) = w_0 + w_1 x_1 + \ldots + w_d x_d = w^T x, \tag{2}$$

where $w=(w_0, x_1, \ldots, w_d)^T$ are the adaptive parameters and $x=(x_1, x_2, \ldots, x_d)$ is the extracted features pattern. Model optimization according to sum-of-squares error minimization yields the following solution, $$w = X^+ t \qquad (3)$$

where rows of matrix X are training patterns, $X^+$ is its pseudo-inverse matrix, and vector $t=(t_1, t_2, \ldots, t_N)^T$ contains the target values corresponding to the training patterns.

C.2. Multilayer Perceptron Networks

MLP networks are models for expressing knowledge using a connectionist paradigm inspired in the human brain. They are composed of multiple simple units or neurons known as perceptrons, which are characterized by an activation function $g_t(\cdot)$. Perceptrons are arranged in several interconnected layers. Each network connection between two of them is associated with a network adaptive parameter or weight ($w_{ij}$). The response of the network to the input pattern is provided by units in the final layer (output layer). The remaining network layers are referred to as hidden layers. Typically, MLP networks with a single hidden layer composed of non-linear perceptrons (i.e., with a non-linear activation function) are implemented since they are capable of universal approximation. The number of units in this layer must be determined by the designer. The configuration of the output layer depends on the specifications of the problem. The proposed regression task aims to approximate a one-dimensional continuous variable representing the AHI. Thus, a single output unit with a linear activation function is used. Accordingly, the network output is given by:

$$y(x, w) = \sum_{j=1}^{N_H} \left\{ w_j g_t \left( \sum_{i=1}^{d} w_{ij} x_i + b_j \right) + b_0 \right\} \qquad (4)$$

where w is the weight vector composed of all the adaptive parameters (weights and biases) in the network, $N_H$ is the number of hidden units, $w_j$ is the weight connecting hidden unit $h_j$ with the output unit, $b_0$ is the bias associated with the output unit, is the weight connecting the input feature i with hidden unit $h_j$ and $b_j$ is its associated bias. Weights are adjusted from samples in the training set during the training or learning process. The aim is to infer the statistical properties of the problem into the network. According to the maximum likelihood principle, weights are chosen in order to minimize the sum-of-squares error function. Second-order non-linear optimization algorithms are used for this purpose.

Weight decay regularization can be applied to control network complexity and increase generalization capability. As stated by the bias-variance trade-off, networks with a large number of adaptive parameters (compared to the size of the training set) may overfit the data. Weight decay favors small weights (smooth mappings) by adding a penalty term to the error function $E_D$. It is equal to the sum of the squares of the network weights.

The MLR model has a unique solution given the training set D. FIG. 10 shows the coefficients $w=(w_0, x_1, \ldots, w_d)^T$ associated to each of the input features according to the MLR equation in. The additional bias term was determined to be $w_0 = 25.75 \text{ h}^{-1}$.

MLP models require a thorough design to achieve high generalization performance. According to the bias-variance trade-off, both excessively simple and complex models will lead to poor generalization due to underfitting and overfitting, respectively. Therefore, model selection is required in order to find the optimum network complexity. It is related to the number and magnitude of network weights. Thus, complexity is influenced by the number of hidden units ($N_H$) and the regularization parameter (v). The performance of several network configurations was compared by varying these parameters. A wide range of values was defined for them in order to analyze their effect on generalization ability: $N_H$ was varied from 2 to 50 units while v values between 0.01 and 100 were evaluated. For each network configuration, the ICC was computed using leave-one-out cross-validation from data in the training set.

Figure 7:
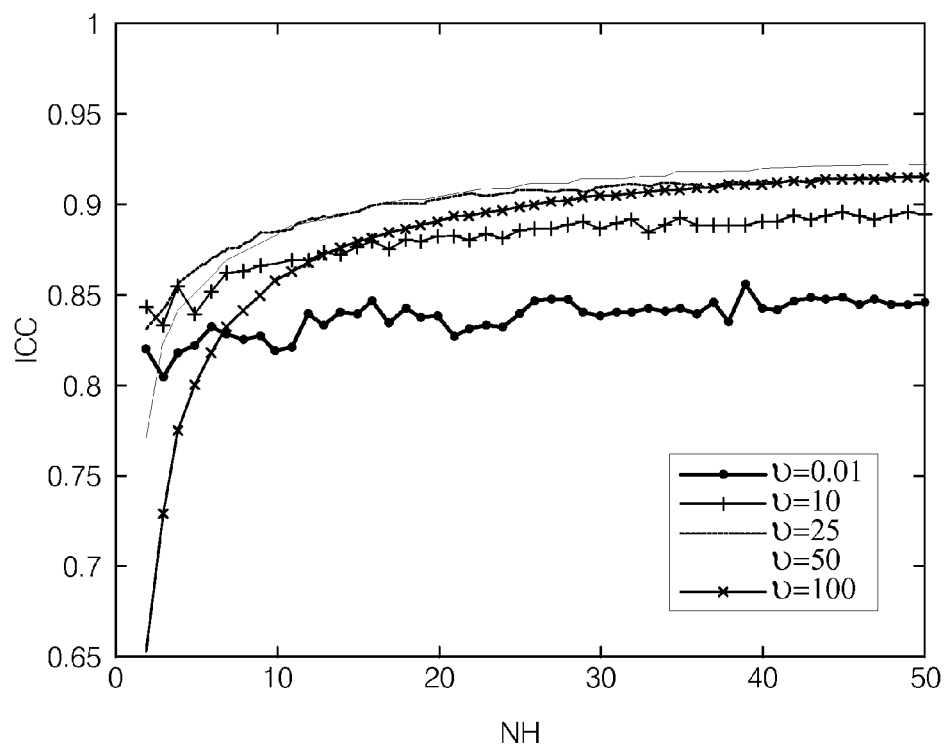

The evolution of ICC is shown in FIG. 7. The performance increased as v varied from 0.01 up to 50, which indicates that configurations with small v may be affected by overfitting. Setting v higher than 50 resulted in lower performance due to an excessive reduction of network complexity. Thus, v was set to 50. For this value, we observed that ICC gradually increased as more hidden nodes were added. However, there was no substantial improvement beyond a given value of $N_H$, which approximately corresponds to $N_H = 40$. Therefore, this number of hidden nodes was selected for the MLP embodiment. Finally, a MLP network with the selected configuration was trained using the complete training set. The scaled conjugate gradient algorithm was used for weight optimization.

C.3. Example Performance Results

A validation study was conducted to evaluate the performance of a particular embodiment of the AHI prediction method, system, and apparatus. MLR and MLP algorithms were assessed on the test set. The results of this assessment study to evaluate a particular embodiment of the computer-implemented method described herein have been reported in scientific the peer-reviewed article entitled "Automated Prediction of the Apnea-Hypopnea Index from Nocturnal Oximetry Recordings" published in IEEE Transactions on Biomedical Engineering. Specifically, a scientific study was conducted to characterize the performance of a particular embodiment of the proposed AHI prediction method. A set of 240 SaO2 signals was available for the assessment study (FIG. 9). The data was divided into training (96 signals) and test (144 signals) sets for model optimization and validation, respectively. Fourteen time-domain and frequency-domain features were used to quantify the effect of SAHS on SaO2 recordings. Regression analysis was performed to estimate the functional relationship between the extracted features and the AHI. Multiple linear regression (MLR) and multilayer perceptron (MLP) neural networks were evaluated.

Figure 8:
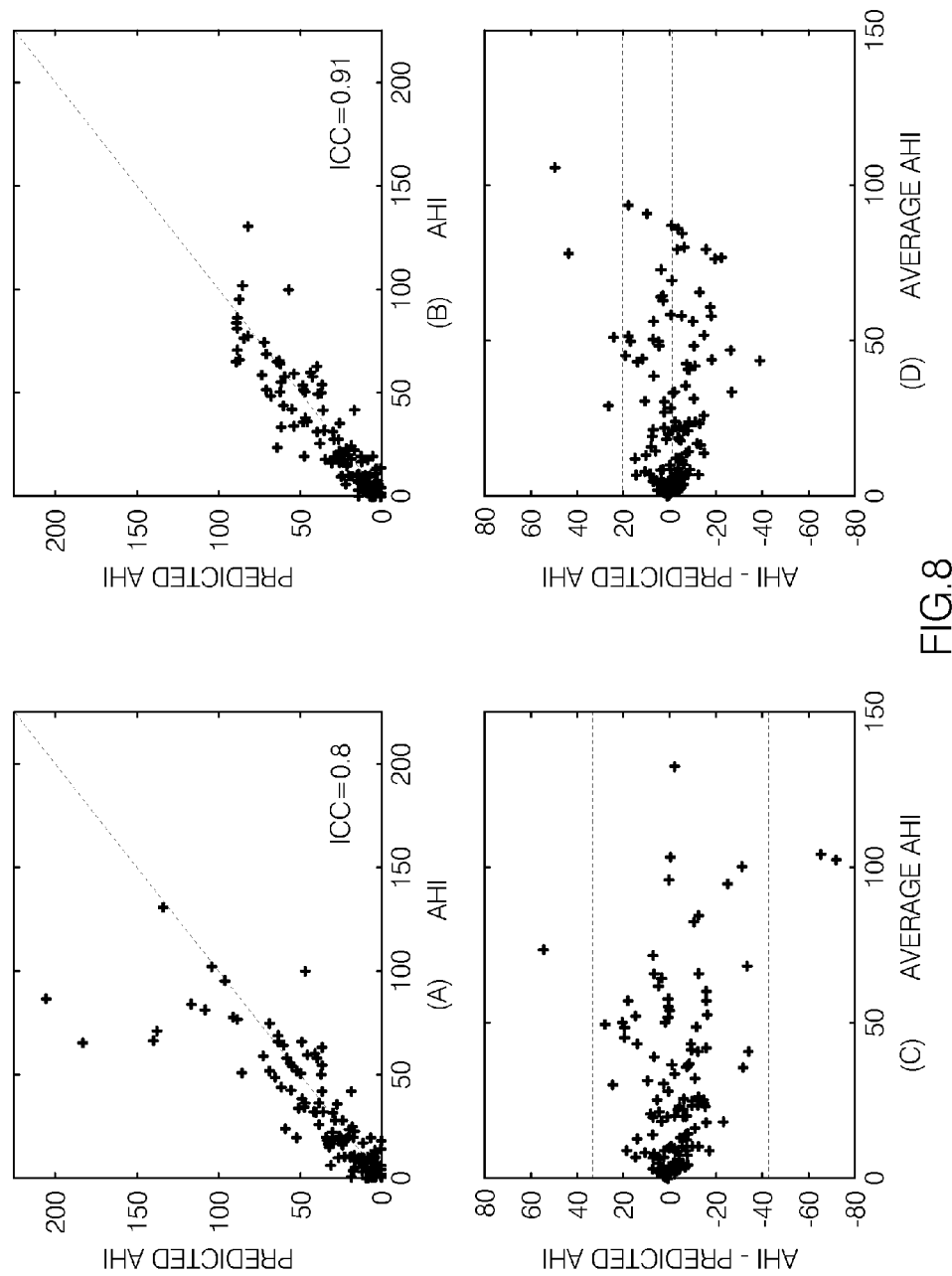

MLR and MLP algorithms were assessed on the test set. From ICC analysis, the MLP network (ICC=0.91) outperformed the MLR model (ICC=0.80). FIG. 8 depicts actual versus predicted AHI as well as Bland-Altman plots for MLR and MLP models. Graphs were derived from AHI estimations computed for subjects in the test set. As reflected by the ICC value, graphic representation of the results shows that more accurate AHI estimations were provided by the MLP network. A smaller deviation from the target AHI (dotted line) can be observed for this model. This behavior is also reflected by Bland-Altman analysis. The mean of the differences between actual and predicted AHI is closer to zero for the MLP model. Furthermore, the scatter of the points is substantially higher for the MLR model, as indicated by the value of the endpoints for the 95% confidence interval. Additionally, the ability of these estimators to rank SAHS severity was evaluated. The predicted AHI was used to assign each subject to one of the following categories: non-SAHS ($0 \text{ h}^{-1} \leq \text{AHI} < 5 \text{ h}^{-1}$), mild-SAHS ($5 \text{ h}^{-1} \leq \text{AHI} < 15 \text{ h}^{-1}$), moderate-SAHS ($15 \text{ h}^{-1} \leq \text{AHI} \leq 30 \text{ h}^{-1}$) and severe-SAHS ($\text{AHI} > 30 \text{ h}^{-1}$). The confusion matrices for MLR and MLP models are shown in FIG.

11. The element (i, j) of the matrix represents the number of times that a class subject was assigned to class j. The results indicate that the MLP network achieved the highest overall performance.

Both regression algorithms were also assessed in a binary classification context in which non-SAHS and SAHS are the two only possible categories. FIG. 12 summarizes the results obtained using an AHI of 5, 10 and 15 $h^{-1}$ as the decision threshold. The MLP network improved the classification capability of the MLR model for all the evaluated thresholds. The highest accuracy of both algorithms was achieved for a decision threshold of 15 $h^{-1}$, which represents a more conservative definition of SAHS. The MLP network provided a correct decision rate of 93.06% whereas the MLR model achieved 88.89%.

The MLP algorithm achieved the highest performance with an intraclass correlation coefficient (ICC) of 0.91. The results of the clinical assessment study show that the proposed MLP-based method could be used as an accurate and cost-effective method for SAHS diagnosis in the absence of PSG.

D. Alternative Embodiments

While particular embodiments have been described, it is understood that, after learning the teachings contained in this disclosure, modifications and generalizations will be apparent to those skilled in the art without departing from the spirit of the disclosed embodiments. It is noted that the disclosed embodiments and examples have been provided merely for the purpose of explanation and are in no way to be construed as limiting. While the methods, systems, apparatuses have been described with reference to various embodiments, it is understood that the words which have been used herein are words of description and illustration, rather than words of limitation. Further, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims.

Those skilled in the art, having the benefit of the teachings of this specification, may effect numerous modifications thereto and changes may be made without departing from the scope and spirit of the disclosed embodiments in its aspects.

Certain specific details are set forth in the above description and figures to provide an understanding of various embodiments disclosed for those of skill in the art. Certain well-known details often associated with medical devices, computing and software technology are not set forth in the following disclosure to avoid unnecessarily obscuring the various disclosed embodiments. Further, those of ordinary skill in the relevant art will understand that they can practice other embodiments without one or more of the details described in the present disclosure. Aspects of the disclosed embodiments may be implemented in the general context of computer-executable instructions, such as program modules, being executed by a computer, computer server, or device containing a processor. Generally, program modules or protocols include routines, programs, objects, components, data structures, hardware executable instructions that perform particular tasks or implement particular abstract data types. Aspects of the disclosed embodiments may also be practiced in distributed computing environments where tasks are performed by remote processing devices (processors, microprocessors, computing systems, FPGAs, programmable ICs, etc) that are linked through a communications network. In a distributed computing environment, program modules and hardware executable instructions may be located in both local and remote storage media such as memory storage devices (including non-transitory storage media). Those skilled in the art will appreciate that, given the description of the modules comprising the disclosed embodiments provided in this specification, it is a routine matter to provide working systems which will work on a variety of known and commonly available technologies capable of incorporating the features described herein. Additionally, the methods described herein can be implemented in a hardware-readable storage medium (including non-transitory computer-readable media) with an executable program stored thereon, wherein said executable program instructs the processing hardware perform the method steps.

The invention claimed is:

1. A method for monitoring sleep apnea severity, comprising:
   (a) analyzing an oxygen saturation signal to extract a plurality of time-domain and frequency-domain metrics based on nonlinear methods that measure irregularity, variability, and complexity of said oxygen saturation signal;
   (b) calculating an oxygen saturation-based Apnea Hyponea Index (AHI) by employing a predetermined functional mapping between said metrics and polysomnography (PSG)-based AHI; and
   (c) displaying an oxygen saturation-based AHI to enable a specialist to monitor sleep apnea severity without requiring PSG.

2. The method for monitoring sleep apnea severity of claim 1, wherein said oxygen saturation signal is nocturnal oxygen saturation.

3. The method for monitoring sleep apnea severity of claim 2, wherein said functional mapping is a multilinear regression model (MLR) or a multilayer perceptron network (MLP).

4. The method for monitoring sleep apnea severity of claim 1, wherein said nonlinear methods that measure irregularity, variability, and complexity of said oxygen saturation signal include approximate entropy (ApEn), central tendency measure (CTM), and Lempel-Ziv complexity (LZC).

5. The method for monitoring sleep apnea severity of claim 4, wherein said time-domain metrics further comprise mean, variance, skewness, and kurtosis.

6. The method for monitoring sleep apnea severity of claim 5, wherein said time-domain metrics are computed by dividing the oxygen saturation signal into sample epochs.

7. The method for monitoring sleep apnea severity of claim 6, wherein said frequency-domain metrics comprise power spectral density (PSD).

8. The method for monitoring sleep apnea severity of claim 7, wherein said frequency-domain metrics further comprise a total power of said oxygen saturation signal, a power measure over a predetermined frequency band, and a most significant frequency component in said predetermined frequency band.

9. The method for monitoring sleep apnea severity of claim 8, wherein said predetermined frequency band is between 0.010 Hz and 0.033 Hz.

10. The method for monitoring sleep apnea severity of claim 9, wherein said MLP is configured to have more than 20 hidden nodes.

11. An apparatus for monitoring sleep apnea severity, comprising:
   (a) a processor configured for 1) analyzing an oxygen saturation signal to extract a plurality of time-domain and frequency-domain metrics based on nonlinear methods that measure irregularity, variability, and complexity of said oxygen saturation signal and 2) calculating an oxygen saturation-based Apnea Hyponea Index (AHI)

by employing a predetermined functional mapping between said metrics and polysomnography (PSG)-based AHI; and (b) an output device configured for displaying an oxygen saturation-based AHI to enable a specialist to monitor sleep apnea severity without requiring PSG.

12. The apparatus for monitoring sleep apnea severity of claim 11, wherein said oxygen saturation signal is nocturnal oxygen saturation.

13. The apparatus for monitoring sleep apnea severity of claim 12, wherein said functional mapping is a multilinear regression model (MLR) or a multilayer perceptron network (MLP).

14. The apparatus for monitoring sleep apnea severity of claim 13, wherein said nonlinear methods that measure irregularity, variability, and complexity of said oxygen saturation signal include approximate entropy (ApEn), central tendency measure (CTM), and Lempel-Ziv complexity (LZC), and wherein said time-domain metrics further comprise mean, variance, skewness, and kurtosis.

15. The apparatus for monitoring sleep apnea severity of claim 14, wherein said time-domain metrics are computed by dividing the oxygen saturation signal into sample epochs.

16. The apparatus for monitoring sleep apnea severity of claim 15, wherein said frequency-domain metrics comprise power spectral density (PSD), a total power of said oxygen saturation signal, a power measure over a predetermined frequency band, and a most significant frequency component in said predetermined frequency band.

17. The apparatus for monitoring sleep apnea severity of claim 16, wherein said predetermined frequency band is between 0.010 Hz and 0.033 Hz.

18. The apparatus for monitoring sleep apnea severity of claim 17, wherein said MLP is configured to have more than 20 hidden nodes.

* * * * *